(12) United States Patent
Rees (10) Patent No.: US 6,204,266 B1
(45) Date of Patent: Mar. 20, 2001

(54) PHARMACEUTICAL, COSMETIC AND/OR FOOD COMPOSITION HAVING ANTI-OXIDANT PROPERTIES

(75) Inventor: Jean-François Rees, Rue des Tilleuls (BE)

(73) Assignee: Universite Catholique De Louvain Halles Universitaires, Louvain-La-Neuve (BE)

( * ) Notice: Subject to any disclaimer, the term of this patent is extended or adjusted under 35 U.S.C. 154(b) by 0 days.

(21) Appl. No.: 08/930,439

(22) PCT Filed: Mar. 11, 1996

(86) PCT No.: PCT/BE96/00024

§ 371 Date: Feb. 17, 1998

§ 102(e) Date: Feb. 17, 1998

(87) PCT Pub. No.: WO96/28160

PCT Pub. Date: Sep. 19, 1996

(30) Foreign Application Priority Data

Mar. 9, 1995 (BE) .................................... 9500207

(51) Int. Cl.[7] ........................ A61K 31/495; A61K 31/50
(52) U.S. Cl. ............................................. 514/249
(58) Field of Search ............................... 514/249

(56) References Cited

U.S. PATENT DOCUMENTS

5,023,181 * 6/1991 Inouye ................................. 435/189

* cited by examiner

*Primary Examiner*—Jerome D. Goldberg
(74) *Attorney, Agent, or Firm*—Knobbe, Martens, Olson & Bear, LLP (57) ABSTRACT

A pharmaceutical, cosmetic and/or food composition includes a pyrazine derivative of formula (I) or (II), and/or a precursor thereof of formula (III). The composition is used for treatment of pathologies associated with prooxidant agents.

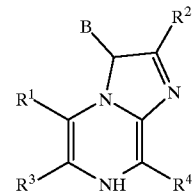

(I)

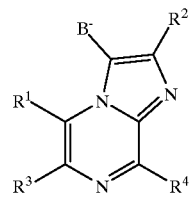

(II)

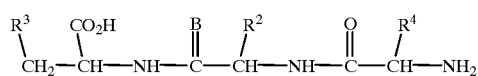

(III)

6 Claims, 11 Drawing Sheets

PHARMACEUTICAL, COSMETIC AND/OR FOOD COMPOSITION HAVING ANTIOXIDANT PROPERTIES

SUBJECT OF THE INVENTION

The present invention relates to a pharmaceutical, cosmetic and/or food composition intended especially for the prevention and/or treatment of pathologies associated with prooxidant agents.

The present invention also relates to the use of the pharmaceutical, cosmetic and/or food composition according to the invention.

TECHNOLOGICAL BACKGROUND AND PRIOR ART UNDERLYING THE INVENTION

Coelenterazine, imidazolopyrazine, constitutes the substrate of bioluminescent reactions in many marine organisms.

In these organisms, the oxidation of coelenterazine by molecular oxygen, a reaction catalyzed by an enzyme (luciferase), is responsible for the light-emitting reaction. Studies have demonstrated the presence of coelenterazine in many non-bioluminescent organisms (Schimomura, Comp. Biochem. Physiol. 86B, pp. 361–363 (1987)).

The synthesis of imidazolopyrazine is known to a person skilled in the art from the following documents: Inoue et al., Chemistry Letters, pp. 299–300 (1980); Tiranishi and Goto, Bulletin of Chemical Society Japanese 63, pp. 3132–3140 (1990); Qi et al., Journal of Chemical Society Perkin Trans 1, pp. 1607–1611 (1982); Mc Capra and Roth, Journal of Chemical Society Chemistry Community, pp. 894–895 (1972); Inoue et al., Chemistry Letters, pp. 141–144 (1975); Inoue et al., Tetrahedron Letters No. 31, pp. 2685–2688 (1977); Qi et al. Journal of Chemical Society Chemistry Community, pp. 1307–1309 (1991); Hori et al., Biochemistry, Vol. 12 No. 22, pp. 4463–4468 (1973); Hart et al., Biochemical and Biophysical Research Communication, pp. 980–986, (1978).

However, none of these documents describes a pharmaceutical, cosmetic or food composition comprising one of these imidazolopyrazine derivatives, or the antioxidant properties of these products, or any other therapeutic application of these products.

Antioxidant molecules such as vitamins, for instance vitamin E (fat-soluble) or cysteine derivatives (water-soluble), are also used already in cosmetic, pharmaceutical and/or food applications. However, these antioxidant molecules have the drawback either of not being water-soluble, or of having an excessively high toxicity as well as an excessively low efficacy.

OBJECTIVES OF THE INVENTION

The present invention is directed towards obtaining a new pharmaceutical, cosmetic and/or food composition advantageously permitting the prevention and/or treatment of pathologies associated with prooxidant agents, and especially a pharmaceutical, cosmetic and/or food composition having anti-inflammatory and/or anticarcinogenic properties.

An additional objective of the present invention is to obtain said pharmaceutical, cosmetic and/or food compositions which shall be characterized by a low toxicity or an absence of toxicity, by a high solubility in a large number of solvents ($H_2O$, alcohols, etc.) and/or lipids and/or by a high stability, especially at acid pH.

CHARACTERISTIC FEATURES OF THE PRESENT INVENTION

The present invention relates to a pharmaceutical, cosmetic and/or food composition comprising a pyrazine derivative of formula and/or its precursor of formula in which formulae B is a radical chosen from the group consisting of X, $X\text{-}SO_3H$, $X\text{-}PO_4$, X-alkyl=O, the said alkyl consisting of 1 to 20 carbon atoms optionally comprising 1 to 10 hetero atoms and in which the carbon atoms can be optionally substituted with any element of the Mendeleev table, preferably an element chosen from the group consisting of H, B, N, O, F, P, S, Cl, As, Se, Br, Te and I, X being an element chosen from the group consisting of O, S, Se and Te;

$R^1$, $R^2$, $R^3$ and $R^4$ are H, radicals chosen from the group consisting of alkyl, alkenyl, alkynyl, aryl, arylalkyl, alkylaryl, heteroaryl, heteroalkyl and hetero(alkylaryl and arylalkyl), preferably consisting of 1 to 20 carbon atoms optionally comprising 1 to 10 hetero atoms and in which the carbon atoms can be optionally substituted with any element of the Mendeleev table, preferably an element chosen from the group consisting of H, B, N, O, F, P, S, Cl, As, Se, Br, Te and I, or chains of formula $(R^5 \times R^6)_n$, where $n \geq 1$, x represents one or more hetero atoms and $R^5$ and $R^6$ are radicals chosen from the group consisting of alkyl, alkenyl, alkynyl, aryl, arylalkyl, alkylaryl, heteroaryl, heteroalkyl and hetero(alkylaryl and arylalkyl), consisting of 1 to 20 carbon atoms optionally comprising 1 to 10 hetero atoms and in which the carbon atoms can be optionally substituted with any element of the Mendeleev table, preferably an element chosen from the group consisting of H, B, N, O, F, P, S, Cl, As, Se, Br, Te and I; and optionally an appropriate pharmaceutical, cosmetic and/or food vehicle.

Preferably, in the pyrazine derivatives according to the invention, $R^1$ is H, $R^2$ and $R^4$ are aryl or alkylaryl groups, preferably consisting of 1 to 20 carbon atoms optionally comprising 1 to 10 hetero atoms and in which the carbon atoms can be optionally substituted with any element of the Mendeleev table, preferably an element chosen from the group consisting of H, B, N, O, F, P, S, Cl, As, Se, Br, Te and I, $R^3$ represents a phenol group or a chain of formula $(R^5 \times R^6)_n$ in which n=1, x represents O, $R^5$ is a phenyl, and $R^6$ is a methyl.

Preferably, the pyrazine derivative of the pharmaceutical, cosmetic and/or food composition according to the invention is chosen from the group consisting of:

3,7-dihydro-2-(p-hydroxybenzyl)-6-(p-hydroxyphenyl)-8-benzylimidazo[1,2-a]pyrazyn-3-one [sic] (CLZN)

3,7-dihydro-2-methyl-6-(p-metoxyphenyl)-8-benzylimidazo[1,2-a]pyrazyn-3-one [sic] (CLZN-7)

3,7-dihydro-2-phenyl-6-(p-metoxyphenyl)-8-benzylimidazo[1,2-a]pyrazyn-3-one [sic] (CLZN-8)

3,7-dihydro-2-methyl-6-(p-hydroxyphenyl)-8-benzylimidazo[1,2-a]pyrazyn-3-one [sic] (CLZN-9)

3,7-dihydro-2-phenyl-6-(p-hydroxyphenyl)-8-benzylimidazo[1,2-a]pyrazyn-3-one [sic] (CLZN-10)

3,7-dihydro-2-benzyl-6-(p-hydroxyphenyl)-8-benzylimidazo[1,2-a]pyrazyn-3-one [sic] (CLZN-11)

and optionally an appropriate pharmaceutical, cosmetic and/or food vehicle.

Another aspect of the present invention relates to the use of the composition according to the invention for the binding of prooxidant agents (free radicals) such as peroxides, superoxides, etc.

The present invention also relates to a method of treatment and/or prevention of pathologies associated with the action of prooxidant agents, especially inflammatory or carcinogenic pathologies, in which the pharmaceutical, cosmetic and/or food composition according to the present invention is administered to a patient.

The pharmaceutical, cosmetic and/or food vehicles according to the invention are vehicles which are appropriate, in particular, for oral administration, for example in the form of lozenges, coated or uncoated, pills, capsules, solutions, essential oils and/or syrups.

Other appropriate pharmaceutical, cosmetic and/or food vehicles can be used, depending on the chosen mode of administration.

In particular, these pharmaceutical, cosmetic and/or food vehicles can be creams or sun oils which are well known to a person skilled in the art, which can coat various parts of the human or animal body in combination with other skin-protecting agents.

In addition, the products of the invention can be readily incorporated in solvents (aqueous media, alcohols, etc.) or lipids (for example in combination with food oils or suntan oils).

The pharmaceutical, cosmetic and/or food compositions according to the invention are prepared according to processes generally used by a person skilled in the art, especially by pharmacists, and can comprise any vehicle or any adjuvant which is pharmaceutically appropriate, solid or liquid, and non-toxic.

The incorporation of the derivatives according to the invention in a pharmaceutical formulation medium can also be envisaged.

The percentage of active product (pyrazine derivatives) in the pharmaceutical vehicle can vary over very wide ranges, limited only by the tolerance and level of acceptance of the product by the patient.

The limits are generally determined by the frequency of administration to the patient.

A final aspect of the present invention relates to the use of the composition according to the invention for the preparation of a medicament intended for the prevention and/or treatment of pathologies associated with the action of peroxidant agents.

In particular, the present invention relates to the use of the composition according to the invention for the preparation of a medicament intended for the prevention and/or treatment of inflammatory or carcinogenic pathologies and/or for the treatment of cancerous tumours.

EXAMPLES.

1. Origin of the antioxidant properties of the pharmaceutical, cosmetic and food composition according to the invention.

The antioxidant properties of imidazolopyrazine derivatives appear to result, on the one hand from the properties of these molecules to react very rapidly with the activated forms of oxygen.

This property could be due to the existence of electron donor (carbonyl) and electron acceptor (nitrogen) groups in the central nucleus of the molecule.

The phenol groups present in the molecules could also constitute (ROS) scavengers.

The main reaction mechanism is considered to be comparable to the one involved in the chemoluminescent oxidation of coelenterazine by molecular oxygen.

On the other hand, these properties might result from the very high instability of the excited product formed during the reaction of ROSs with imidazolopyrazines.

In effect, contrary to other known substances displaying antioxidant activity, the reaction product is not a stable and unreactive radical. On the contrary, the excited product formed is considered to be characterized by a very great instability. The latter is such that these products appear to disintegrate instantaneously by rupture of the imidazolopyrazine nucleus; a part of the destructive energy of the ROSs is dissipated in the form of light, while the remainder is liberated in the form of thermal radiation.

The results below indicate the existence of a positive cooperative interaction between the imidazolopyrazines and the cytosolic superoxide dismutase (Cu-Zn form) of cells.

This behaviour is demonstrated in experiments that enable the reactivity of imidazolopyrazines with the superoxide anion to be measured. This method is based on the capacity of imidazolopyrazines to react with the superoxide anion, emitting light.

In these experiments, a constant level of superoxide anion is generated by an enzymatic method, by reacting xanthine oxidase with hypoxanthine in the presence of oxygen. This reaction is carried out in the presence of increasing concentrations of superoxide dismutase (Cu-Zn superoxide dismutase), which will compete with the imidazolopyrazine for the superoxide anion and hence modify the maximum light intensity produced.

The maximum light intensity, measured by a luminometer during the competition reaction, is linked to the ratio in [sic] imidazolopyrazine and superoxide dismutase concentrations, as well as to that of the respective rate constants.

Consequently, knowing the rate constant of the reaction of the competing antioxidant with the superoxide anion ($K_3$), the rate constant of the reaction of the imidazolopyrazine with the superoxide anion ($K_2$) may be calculated:
$I_O$=light intensity observed in the absence of the competitor
I=light intensity observed in the presence of the competitor
SOD=superoxide dismutase
IMPZ=imidazolopyrazine $$I_0/I = 1 + \left\{ K_3 \bigg/ \left( K_1[O_2^-] - K_2 \left[ \frac{IMPZ}{K_1} \right] \right) \right\} [SOD] \quad (1)$$

$$2\,O_2^- \Rightarrow O_2 + O_2^{2-}$$

$$IMPZ + O_2^- \xRightarrow{K_2} \text{amidopyrazine} + h\upsilon \quad (2)$$

$$SOD + 2\,O_2^- \xRightarrow{K_3} O_2 + O_2^{2-} + SOD \quad (3)$$

By carrying out this experiment at two imidazolopyrazine concentrations, it is possible to eliminate $K_1\,[O_2^{2-}]$ corresponding to the spontaneous disproportionation reaction of $O_2^{2-}$. The slopes A and B of the straight lines linking $I_O/I$ [sic] to the superoxide dismutase concentration are:

$$A = K_3/(K_1[O_2^-] + K_2[IMPZ]_1) \quad \text{1st concentration of } IMPZ$$

and $$A = K_3/(K_1[O_2^-] + K_2[IMPZ]_1) \quad \text{2nd concentration of } IMPZ$$

and then $$K_2 = K_3/([IMPZ]_1 - [IMPZ]_2)/(1/A) - 1/B)$$

When the imidazolopyrazine concentration is increased, the slope of the relationship linking $I_O/I$ [sic] to the superoxide dismutase concentration should decrease.

Figure 1:
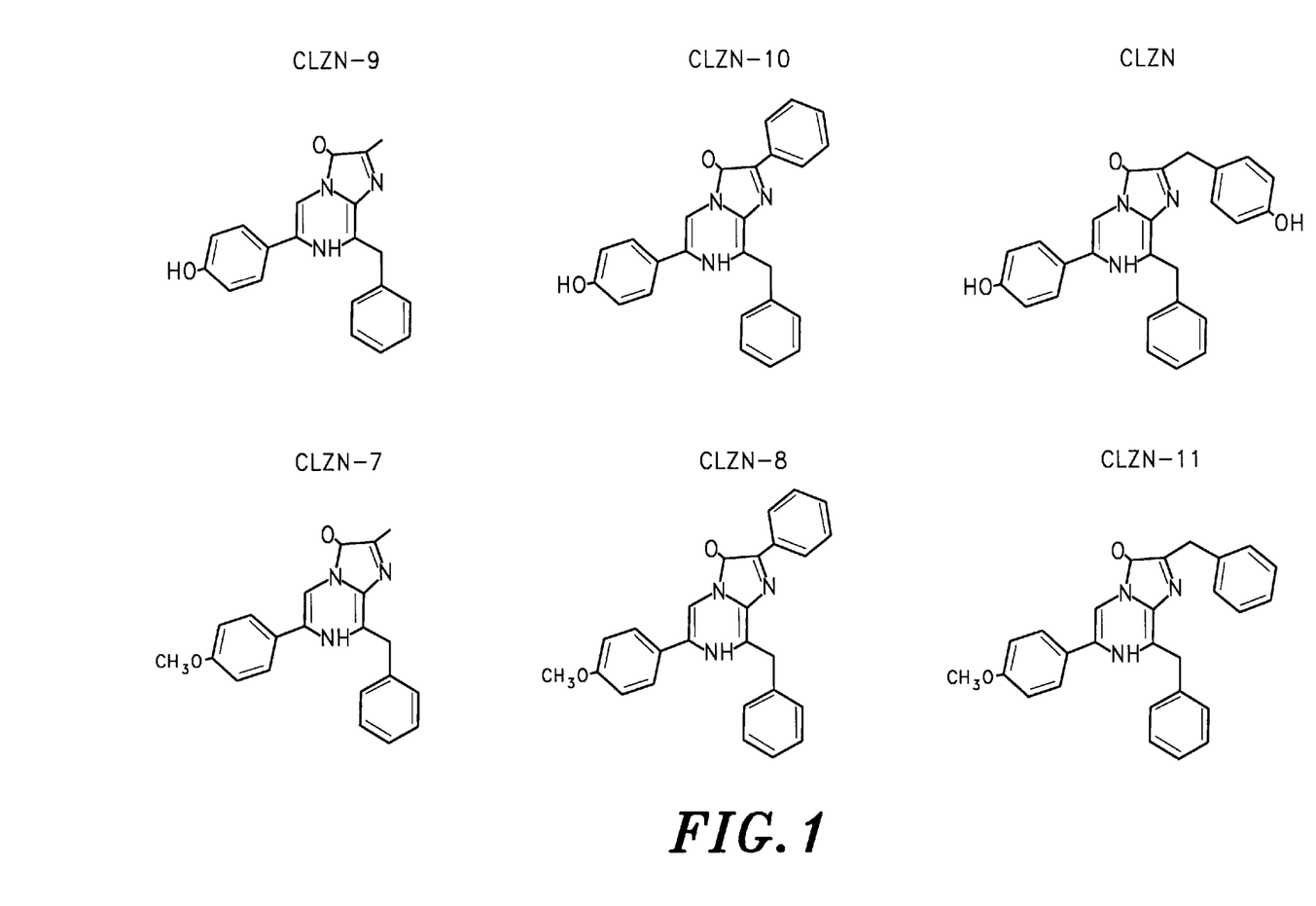
FIG. 1 depicts the structure of the imidazolopyrazine derivatives used in the pharmaceutical and food composition according to the invention.
Figure 2:
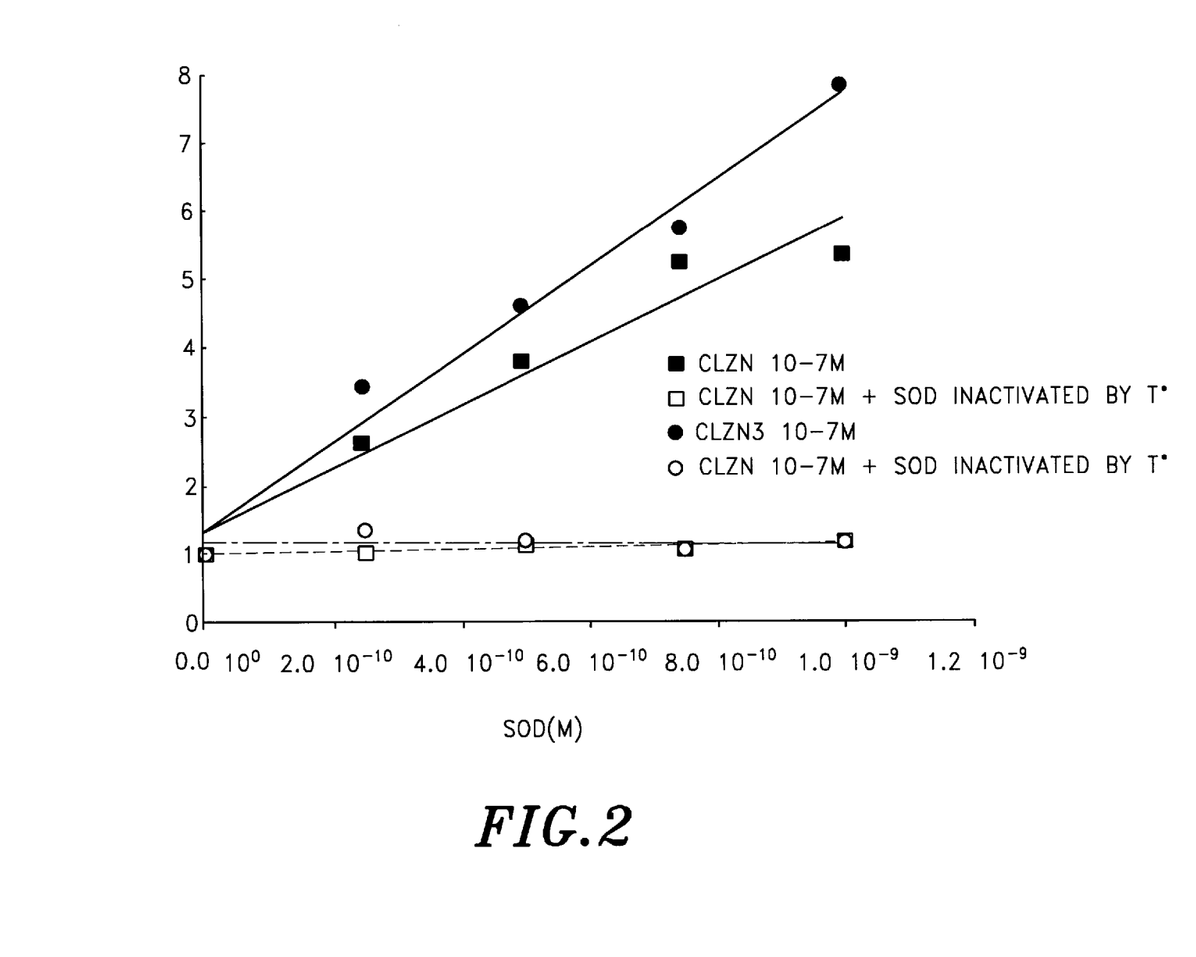
FIG. 2 depicts the relationship linking the superoxide dismutase (SOD) concentration and the ratio of the intensities measured in the absence and in the presence of superoxide dismutase ($I_O/I$) for two coelenterazine (CLZN) concentrations. In this figure, the results of the same experiment carried out when the superoxide dismutase is heat-denatured are also presented.
Figure 3:
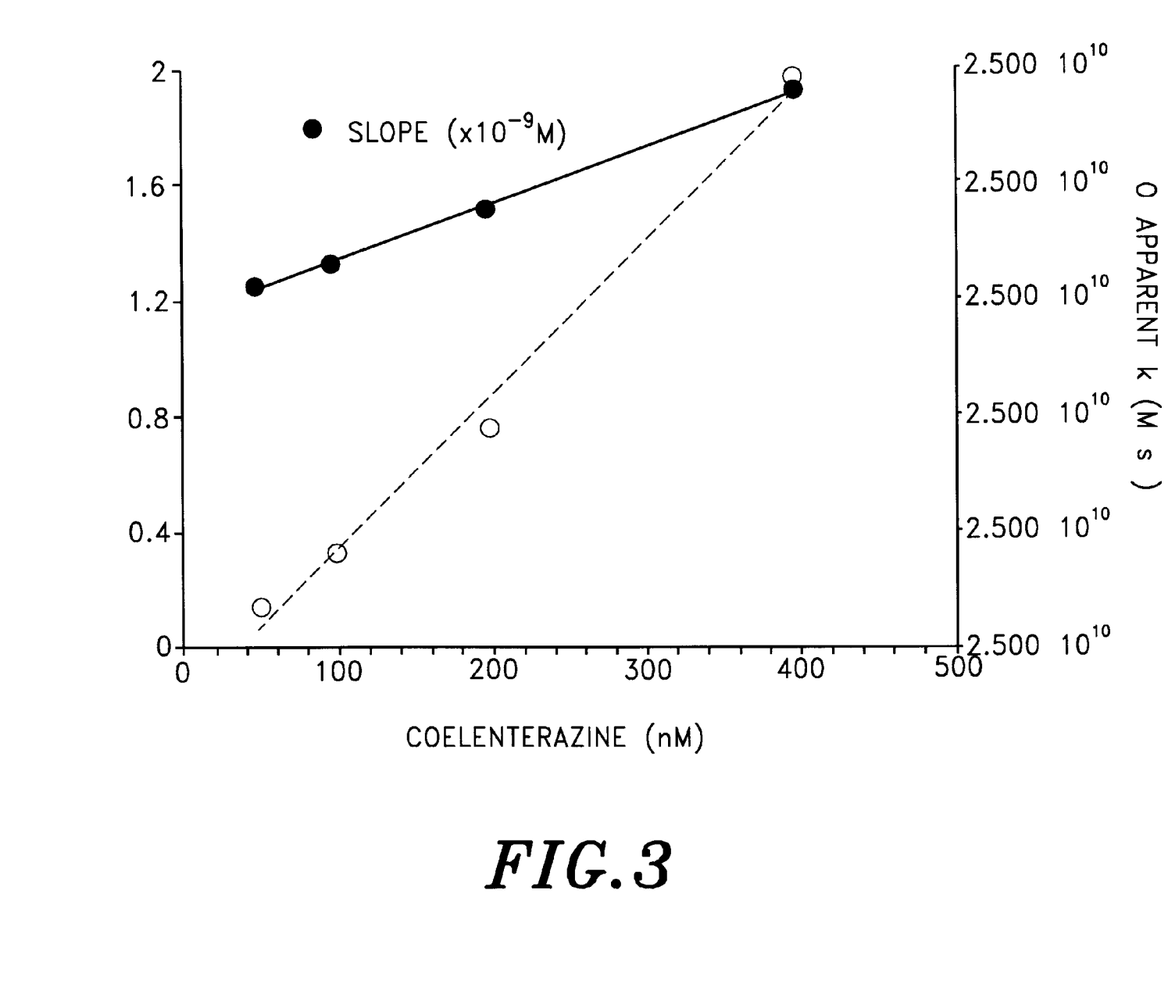
FIG. 3 depicts the change in the slope of the relationship linking the superoxide dismutase concentration and $I_O/I$ and in the rate constant $K_{SOD}$ as a function of the coelenterazine concentration.

These experiments revealed a reverse behaviour, that is to say a rise in the slope for higher imidazolopyrazine concentrations (FIG. 2). This demonstrates a linear relationship between the coelenterazine concentration and the slope of the straight line (FIG. 3). This rise in slope may be interpreted as an increase in the apparent rate constant of the superoxide dismutase.

Thus, when the coelenterazine concentration is multiplied by 8 (from 50 to 400 nM), the rate constant $K_{SOD}$ rises from $2 \times 10^9$ to $2.5 \times 10^{10}$, equivalent to a 12.5-fold increase. This effect was observed for two other imidazolopyrazines tested (CLZN-9 and -10). The magnitude of the increase in $K_{SOD}$ appears to be achieved in proportions similar to those of coelenterazine.

Figure 4:
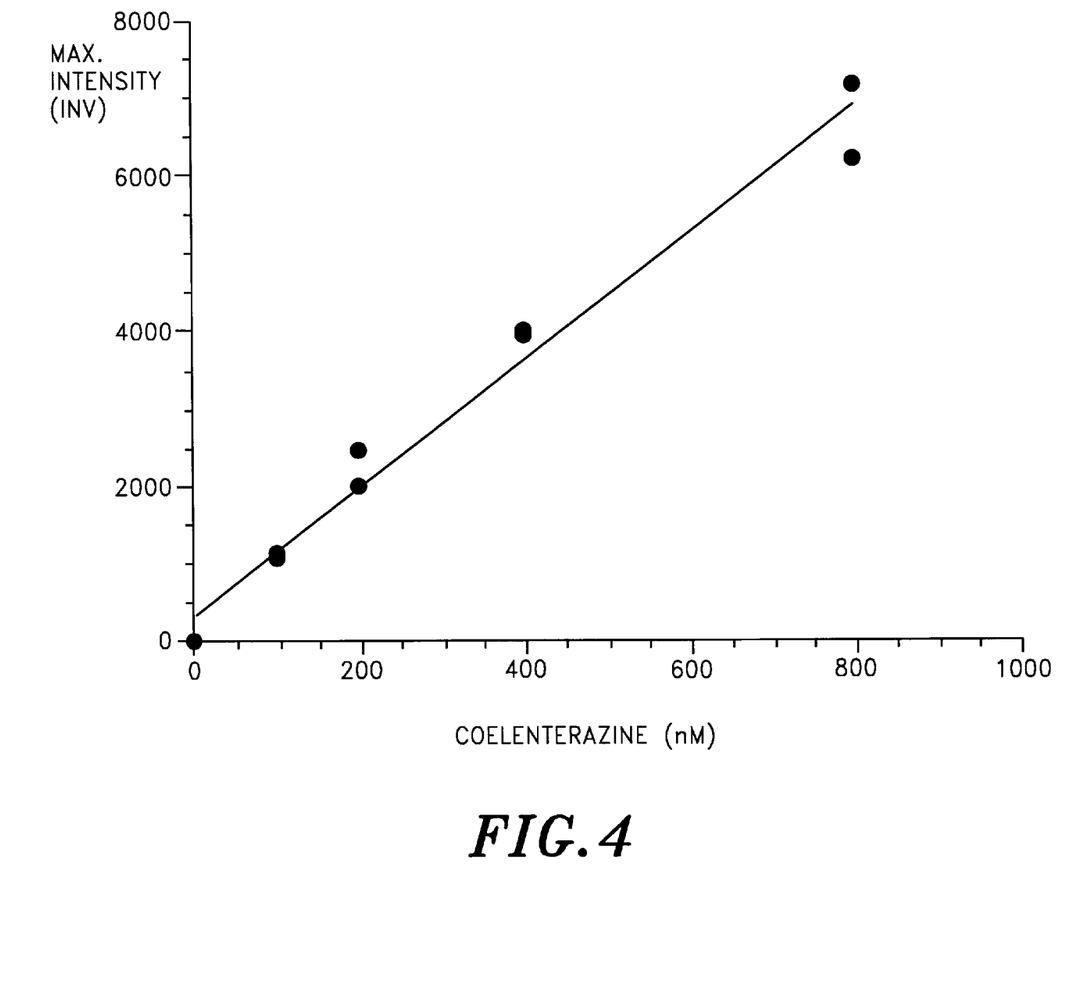
FIG. 4 depicts the linear relationship between the coelenterazine concentration and the maximum intensity of the luminescence brought about by the superoxide anion under our experimental conditions.
Figure 5:
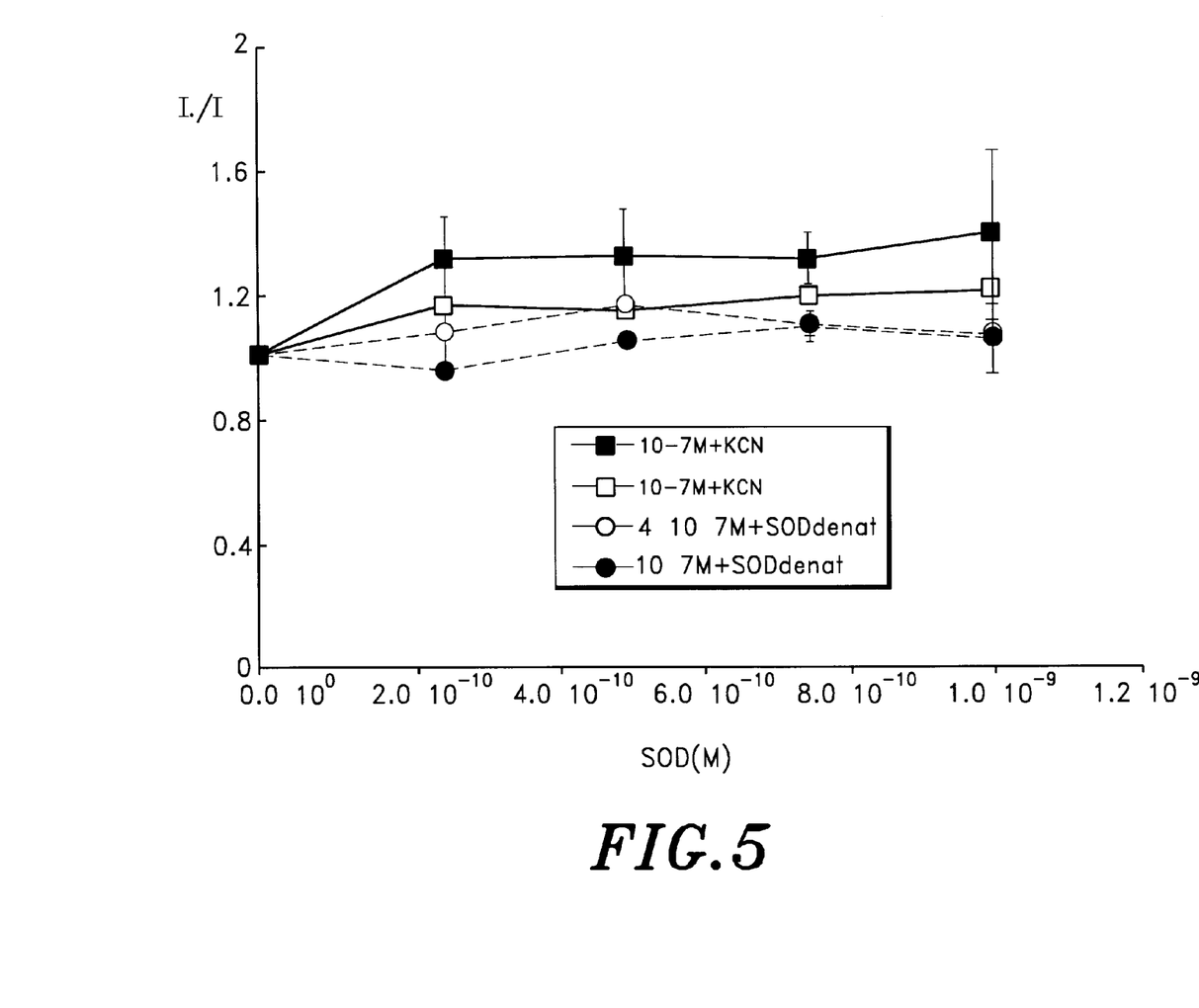
FIG. 5 depicts the inactivation of superoxide dismutase by $10^{-2}$ M KCN. The enzyme activity is completely inhibited by KCN, and no. observable difference remains between the two coelenterazine concentrations ($10^{-7}$ and $4\times10^{-7}$ M).
Figure 6:
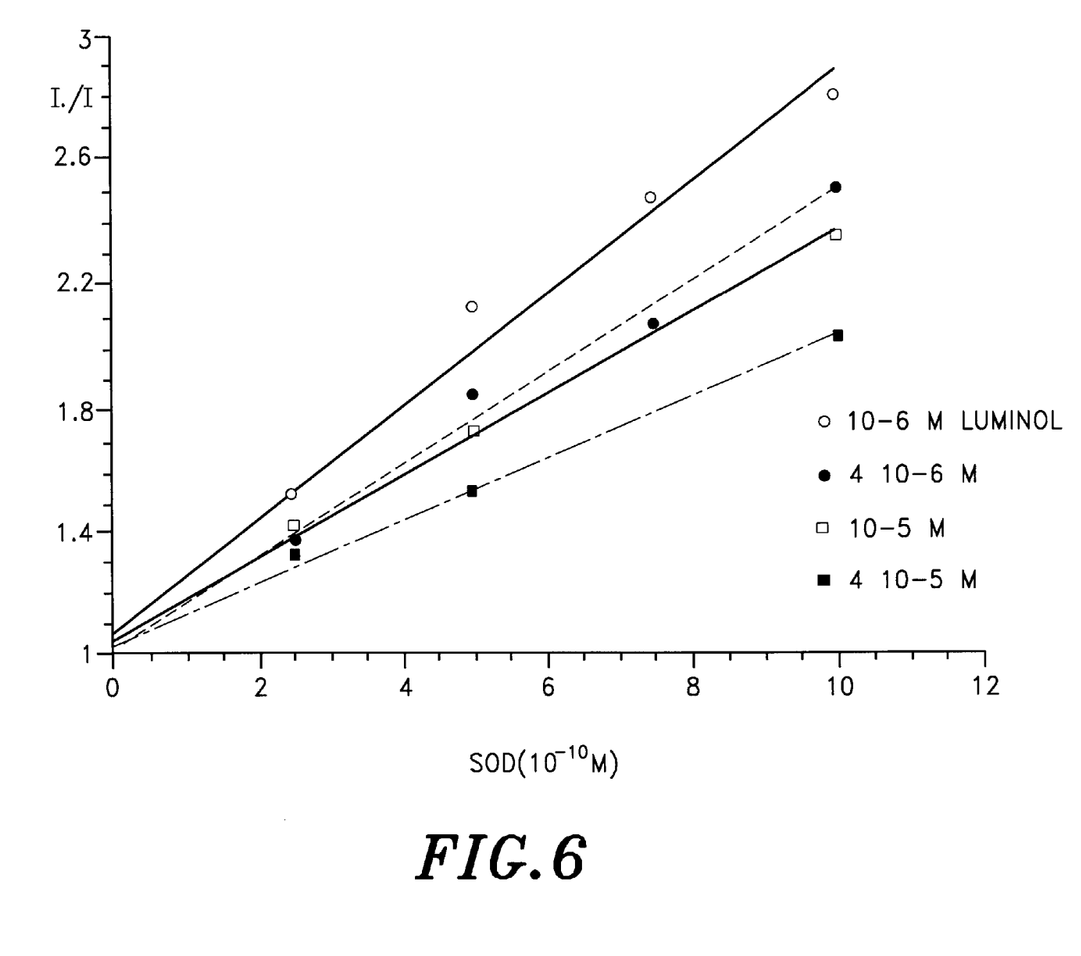
FIG. 6 depicts the influence of the luminol concentration on the slope of the relationship linking the superoxide dismutase concentration and the ratio of the intensities $I_O/I$.

Various controls were carried out in order to verify that the results are not due to an artefact. These include:

a test of linearity between the imidazolopyrazine concentration and the measured light intensity (FIG. 4);

heat denaturation of the superoxide dismutase used shows that the reduction in magnitude of light production on reacting the imidazolopyrazines with the superoxide anion does indeed result from an enzyme activity and not from the presence of metallic contaminants (FIG. 2);

the inactivation of superoxide dismutase by cyanide confirms that the enzyme activity does indeed correspond to superoxide dismutase and not to a protein contaminating the commercial sample (FIG. 5);

lastly, identical experiments were carried out with luminol, a chemoluminescent molecule that reacts with the superoxide anion, which revealed a behaviour of this product in accordance with theoretical predictions, that is to say a regular decrease in the slope when the luminol concentration is increased (FIG. 6).

Consequently, the antioxidant and consequently anticarcinogenic properties of a pharmaceutical, cosmetic or food composition comprising imidazolopyrazine derivatives are completely unexpected, since the binding of superoxide dismutase by the imidazolopyrazine derivatives of the composition according to the invention is specific and is not observed with other chemoluminescent molecules such as luminol.

In view of the importance of superoxide dismutase in combating oxidative stress (see Fridovitch I, Journal of Biological Chemistry 264 (1989), pp. 7761–7764), the action of the imidazolopyrazine derivatives on this enzyme would strengthen the antioxidative defences of the cells, endowing them as a result with better protection against prooxidant agents.

2. In vitro toxicity.

The low toxicity of the pharmaceutical, cosmetic or food composition of the invention for human cells is demonstrated in the experiments which follow.

Each of the imidazolopyrazine derivatives tested was applied to human fibroblasts (MRC5) in culture. The doses of the compounds ranged from $10^{-8}$ to $10^{-4}$ M. These compounds were applied 48 hours after the cells were inoculated into wells (volume=150 μl; 3000 cells per well).

After a further 24 hour period, the culture medium is renewed, the cells are incubated for 72 hours and their level of survival and of growth is evaluated by measuring the total protein contents in each well (Biorad). The results show that the imidazolopyrazine derivatives have little or no toxicity for these cells. Only the derivative CLZN-11 displays a significant toxicity for a concentration of 0.1 mM.

However, the slight toxicity of these derivatives at a concentration of $10^{-4}$ M is explained by the negative action of the 1% ethanol used to solubilize these derivatives. Neither of the two degradation products of the derivatives (CLMN-4 and -5) is toxic for the cells.

Figure 7:
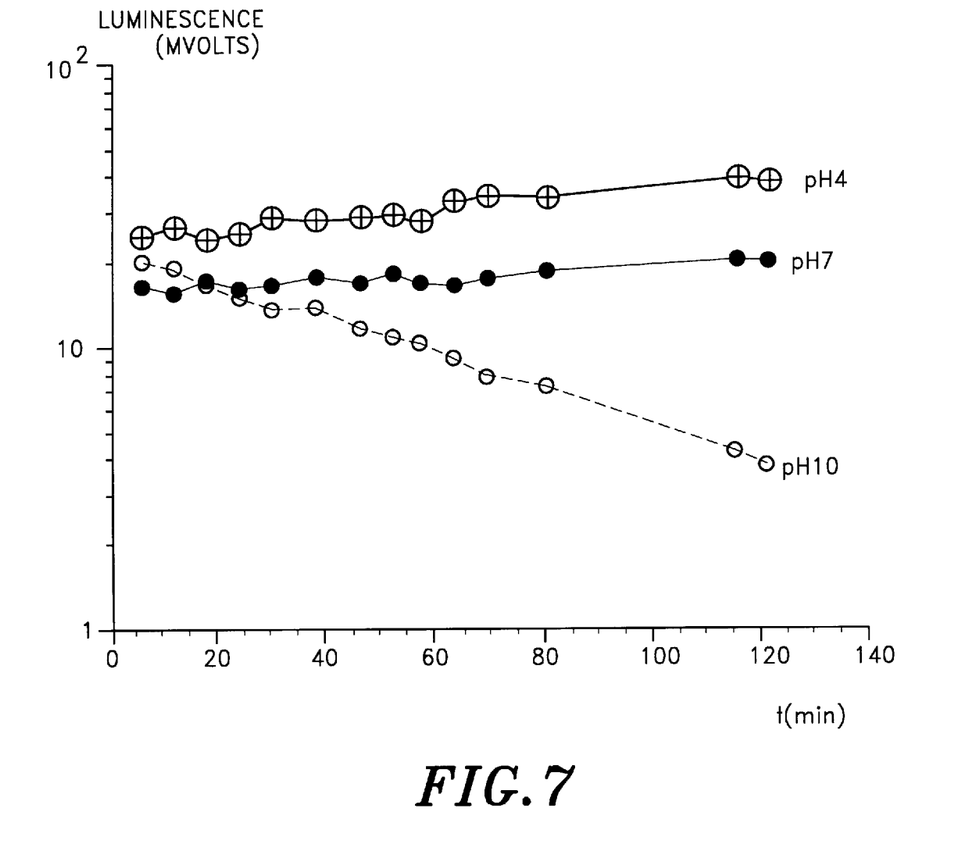
FIG. 7 depicts the stability of the derivative 10 in an aqueous medium. Three $10^{-5}$ M solutions of CLZN-10 were prepared in citrate (pH 4), phosphate (pH 7) and glycine (pH 10) buffers. Aliquots of these solutions were sampled regularly and the CLZN-10 assayed by luminescence in DMSO.

In comparison with coelenterazine, derivatives comprising additional phenyl groups display better stability. While the stability of coelenterazine is only a few hours in an aqueous medium and irrespective of the pH, the products derived from it display excellent stability at acid and neutral pH, while their half-life is in the region of 60 minutes at alkaline pH (FIG. 7).

Similar in vitro toxicity tests were performed on other mammalian (porcine, human, etc.) cell types.

Figure 11:
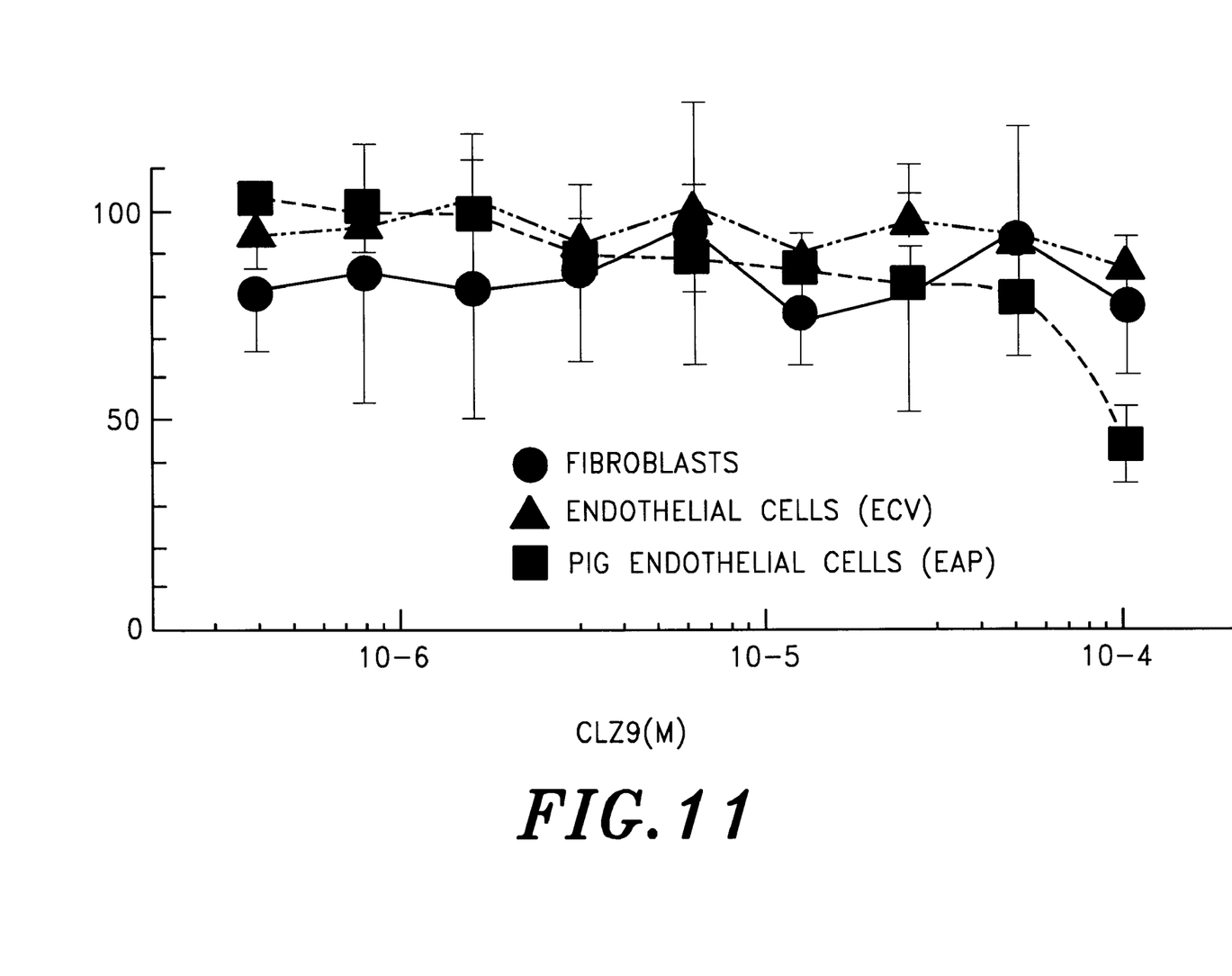
FIG. 11 depicts the percentage survival of different cell types as a function of increasing doses of CLZ-9 (M).

FIG. 11 depicts the percentage survival of different cell types (fibroblasts, human (ECV) or pig (EAP) endothelial cells) as a function of increasing doses of CLZ-9 (molar). A toxic effect of the products can possibly be observed on a certain cell type at high concentrations ($10^{-4}$ M in pigs).

3. In vivo toxicity.

Tests showed that coelenterazine (CLZN) (at a dose of 20 μg/kg and after 5 intraperitoneal injections) is not toxic for mice (the survival is 100% and no growth retardation is observed).

|  | Survival | Weight (in grams) after | | |
|---|---|---|---|---|
|  |  | 0 day | 6 days | 30 days |
| Control mice (6 males) | 6/6 | 13.13 ± 1.6 | 18.65 ± 1.75 | 30.82 ± 1.28 |
| Mice treated with the comp. according to the inv. (5 males) | 5/5 | 16.19 ± 1.93 | 22.82 ± 1.82 | 31.57 ± 1.75 |

4. Reactivity of the compounds with activated oxygen species.

The reactivity of coelenterazine and of the derivatives of the invention with singlet oxygen was measured by pulsed photolysis. The results demonstrate the exceptional reactivity of these compounds, reaction rates reaching $2-30 \times 10^8$ $M^{-1} S^{-1}$. These rate constants are close to the theoretical maxima, taking account of the rate of diffusion of singlet oxygen in the reaction medium, and are equal to or greater than those of most of the known antioxidant agents.

5. Antioxidant properties on fibroblasts.

Figure 8:
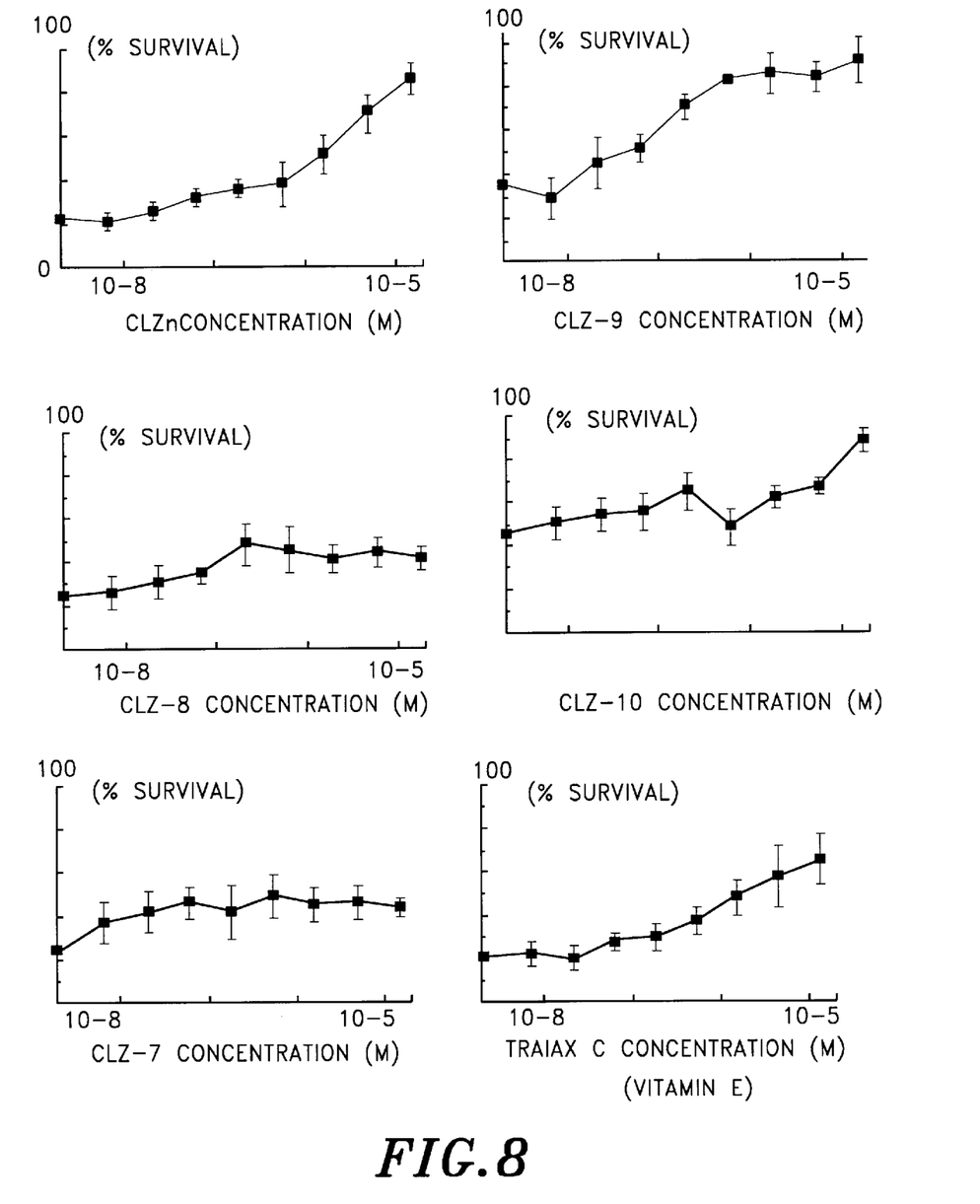
FIGS. 8 and 9 depict the percentage cellular survival of human fibroblasts subjected to an oxidative stress inducer in the presence of increasing doses of derivatives according to the invention, with (FIG. 9) or without (FIG. 8) serum.

Human fibroblasts were subjected to an oxidative stress inducer (tert-butyl hydroperoxide (t-BHP)) for 6 to 12 hours in the absence and in the presence of increasing doses of coelenterazine and its derivatives. Cellular survival after exposure to t-BHP ($10^{-4}$ M) for 10 hours is 20 to 30%. The addition of coelenterazine and its derivatives to the incubation medium improves very significantly (* $p<0.05$; ** $p<0.01$) the survival of the t-BHP-treated cells. The attached FIGS. 8 and 9 present the results obtained with the compositions according to the invention.

Figure 9:
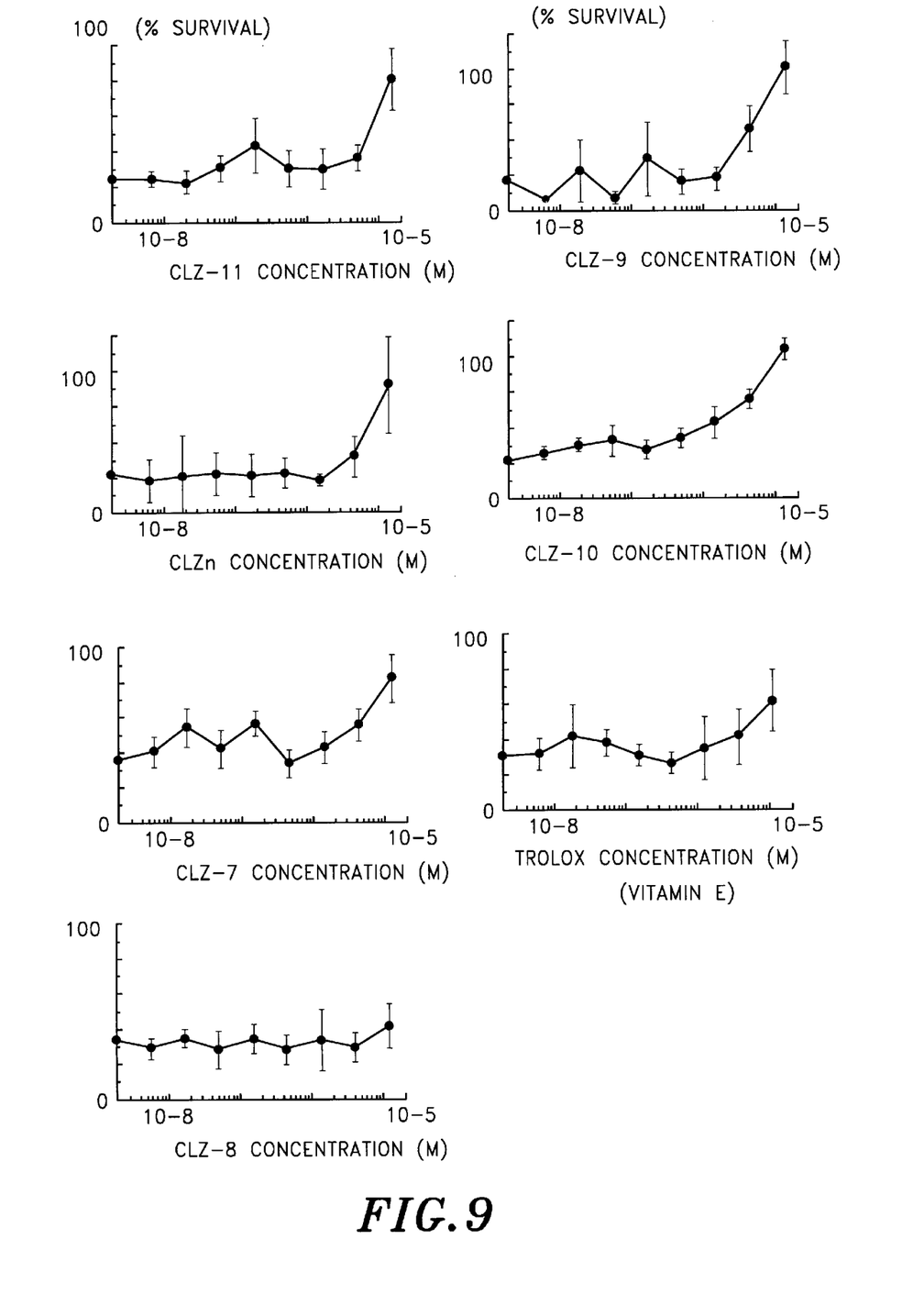

The same experiments in which serum is also added to the medium are depicted in FIG. 9.

The most advantageous results are obtained with the derivative CLZ-9. The improvement is already significant from $2 \times 10^{-8}$ M, while protection is total at $10^{-6}$ M.

In the same experimental series, the efficacy of vitamin E (α-tocopherol) (Troxol®), a major antioxidant of animal cells, was compared. The results indicate that coelenterazine and the derivative CLZ-9 possess an antioxidant activity equivalent to (CLZN) or greater than (CLZ-9) vitamin E. These experiments were also carried out in the presence of serum (10%) in the culture medium, since serum is known to reduce greatly the life of antioxidants. Under these conditions, the efficacy of the compounds according to the invention in protecting the cells is retained, and protection reaches 80 to 100% at the highest concentrations, while it reaches only 60% in the case of vitamin E.

6. Cosmetic composition suitable for skin hygiene.

| Composition | Percentage by weight |
|---|---|
| Oily phase | |
| BRIJ 721 (Stéarate 21 ®) buffer | 4.00 |
| Cetyl alcohol | 10.00 |
| Mineral oil | 5.00 |
| Propyl para-hydrobenzoate [sic] | 0.02 |
| Aqueous phase | |
| Carbopol 934 ® | 0.10 |
| Sodium hydroxide (10% solution) | 0.10 |
| Methyl para-hydrobenzoate [sic] | 0.18 |
| Derivatives according to the invention | 0.05 to 5.00 |
| Demineralized water | 75.60 to 80.05 |
| Total | 100.00 |

The cosmetic composition according to the invention may be applied in cream form directly to the patient's skin.

The derivatives according to the invention may also be incorporated in the oily phase of the cosmetic composition instead of being dissolved in the aqueous composition.

7. Food composition according to the invention.

The composition according to the invention is added to an oily phase of a food composition, especially in spreads of the minarine or margarine type.

| Composition | Percentage by weight |
|---|---|
| Oily phase | |
| Butter | 12.50 |
| Mixture of oils which has incorporated derivatives according to the invention | 10.00 |
| Monoglycerides | 0.47 |
| Lecithin | 0.20 |
| β-Carotene (30% in oil) | 0.03 |
| Aqueous phase | |
| Water | 59.70 |
| Sugar or sugar substitute | 0.15 |
| Gelatin | 1.5 |
| Salt | 0.5 |
| Potassium sorbate | 0.10 |
| Lactic acid | <0.10 |

Method of production

Oily phase: the powdered ingredients are incorporated in the mixture of oils, to which melted butter and, where appropriate, a colorant are added. This fatty phase is stored at 55° C.

Aqueous phase: the gelatin is dispersed in water at 80° C., the other ingredients are added and the pH is adjusted to 5 with lactic acid. The ingredients are mixed until a homogeneous mass is obtained, and the aqueous mixture is stored at 55° C.

The aqueous phase is then incorporated slowly and with vigorous stirring in the fatty dispersion at 55° C. The product is then homogenized at 200 bars and then allowed to cool rapidly to 12° C. The product is packaged in cartons and stored refrigerated before administration to a patient.

Other examples of cosmetic or food compositions can comprise the compounds according to the invention in combination with other adjuvants, which can be incorporated in the aqueous phase or the oily phase of the cosmetic and/or food compositions according to the invention.

Figure 10:
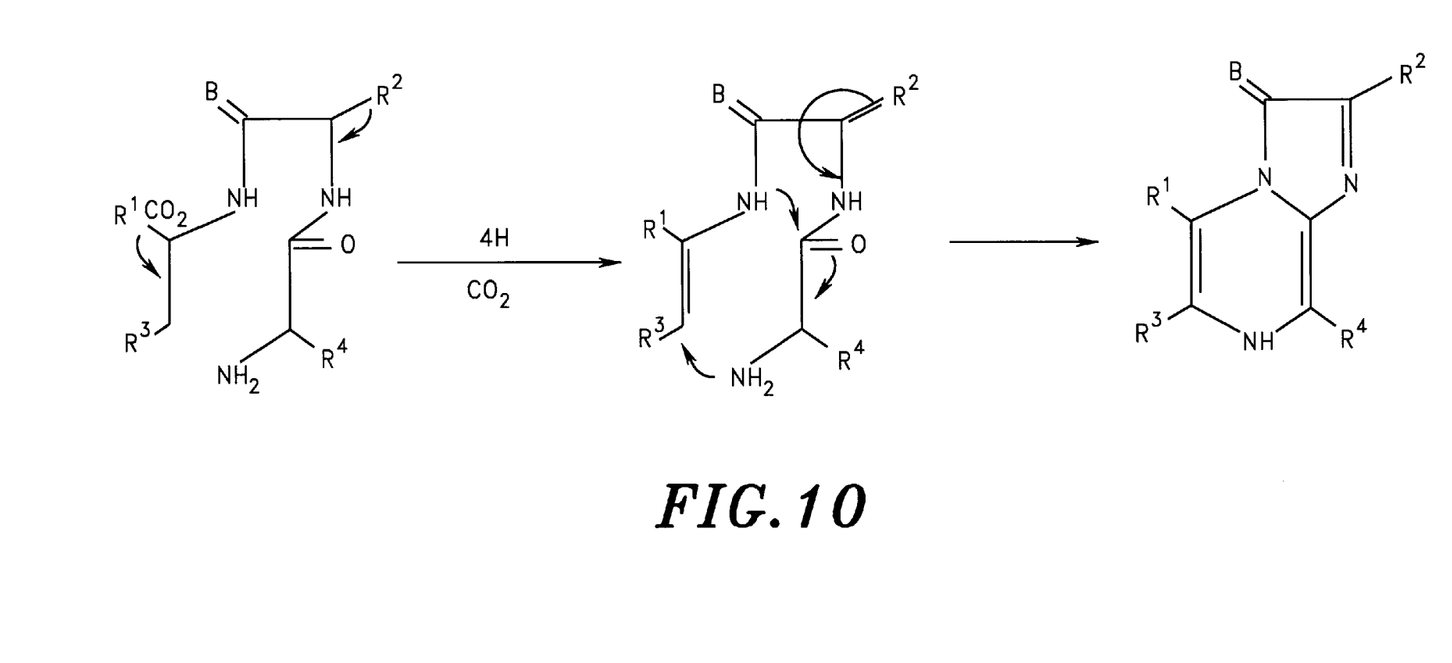
FIG. 10 depicts diagrammatically the conversion of a precursor of the derivative according to the invention to a derivative of the invention.

The inventors have also depicted, in FIG. 10, the conversion of a precursor of a derivative according to the invention to a pyrazine derivative.

As is seen in FIG. 10, the precursor of the invention is capable of also binding free radicals so as to obtain the derivative according to the invention, which is still active and also capable of binding free radicals.

Unexpectedly, the Applicant also observed that the derivatives of the invention possess antitumour properties, especially with respect to mammary carcinoma at low concentrations.

Hence the derivatives of the invention have a lethal effect on cancer cell lines at concentrations at which they are not toxic for normal cells.

What is claimed is:

1. A method for treating inflammation or cancer sensitive to the compounds below in a recipient in need thereof, comprising administering a pyrazine derivative of formula I or II to the recipient in an amount effective to exhibit an antioxidant effect in the recipient, wherein formula I has the following structures:

(I)

(II)

wherein B is a radical selected from the group consisting of X, X-SO$_3$H, X-PO$_4$ and X-alkyl=O in which X is an element selected from the group consisting of O, S, Se and Te; and R$^1$ is H, R$^2$ is selected from the group consisting of methyl, phenyl, p-hydroxybenzyl, and benzyl, R$^3$ is p-hydroxyphenyl or p-methoxyphenyl and R$^4$ is benzyl and substituted radicals of the foregoing.

2. A method according to claim 1, wherein the pyrazine derivative is selected from the group consisting of: 3,7-dihydro-2-(p-hydroxybenzyl)-6-(p-hydroxyphenyl)-8-benzylimidazo[1,2-a]pyrazyn-3-one [sic], 3,7-dihydro-2-methyl-6-(p-metoxyphenyl)-8-benzylimidazo[1,2-a]pyrazyn-3-one [sic], 3,7-dihydro-2-phenyl-6-p-metoxyphenyl)-8-benzylimidazo[1,2-a]pyrazyn-3-one [sic], 3, 7-dihydro-2-methyl-6-(p-hydroxyphenyl)-8-benzylimidazo[1,2-a]pyrazyn-3-one [sic], 3,7-dihydro-2-phenyl-6-(p-hydroxyphenyl)-8-benzylimidazo[1,2-a]pyrazyn-3-one [sic], and 3,7-dihydro-2-benzyl-6-(p-hydroxyphenyl)-8-benzylimidazo[1,2-a]pyrazyn-3-one [sic].

3. A cosmetic composition comprising a base cosmetic and, in an amount effective to exhibit an antioxidant effect in a recipient, a pyrazine derivative of formula:

(I)

(II)

wherein B is a radical selected from the group consisting of X, X-SO$_3$H, X-PO$_4$ and X-alkyl=O in which X is an element selected from the group consisting of O, S, Se and Te; and R$^1$ is H, R$^2$ is selected from the group consisting of methyl, phenyl, p-hydroxybenzyl, and benzyl, R$^3$ is p-hydroxyphenyl or p-methoxyphenyl and R$^4$ is benzyl and substituted radicals of the foregoing.

4. A cosmetic composition according to claim 3, wherein the pyrazine derivative is selected from the group consisting of: 3,7-dihydro-2-(p-hydroxybenzyl)-6-(p-hydroxyphenyl)-8benzylimidazo[1,2-a]pyrazin-3-one [sic], 3,7-dihydro-2-methyl-6-(p-metoxyphenyl)-8-benzylimidazo[1,2-a] pyrazyn-3-one [sic], 3,7-dihydro-2-phenyl-6-(p-metoxyphenyl)-8-benzylimidazo[1,2-a]pyrazyn-3-one [sic], 3,7-dihydro-2-methyl-6-(p-hydroxyphenyl)-8-benzylimidazo[1,2-a]pyrazyn-3-one [sic], 3,7-dihydro-2-phenyl-6-p-hydroxyphenyl)-8-benzylimidazo[1,2-a] pyrazyn-3-one [sic], and 3,7-dihydro-2-benzyl-6-(p-hydroxyphenyl)-8-benzylimidazo[1,2-a]pyrazyn-3-one [sic].

5. A food composition comprising a base food and, in an amount effective to exhibit an antioxidant effect in a recipient, a pyrazine derivative of formula:

(I)

(II)

wherein B is a radical selected from the group consisting of X, X-SO$_3$H, X-PO$_4$ and X-alkyl=O in which X is an element selected from the group consisting of O, S, Se and Te; and $R^1$ is H, $R^2$ is selected from the group consisting of methyl, phenyl, p-hydroxybenzyl, and benzyl, $R^3$ is p-hydroxyphenyl or p-methoxyphenyl and $R^4$ is benzyl and substituted radicals of the foregoing.

6. A food composition according to claim 5, wherein the pyrazine derivative is selected from the group consisting of: 3,7-dihydro-2-(p-hydroxybenzyl)-6-(p-hydroxyphenyl)-8benzylimidazo[1,2-a]pyrazyn-3-one [sic], 3,7-dihydro-2-methyl-6-(p-metoxyphenyl)-8-benzylimidazo[1,2-a]pyrazyn-3-one [sic], 3,7-dihydro-2-phenyl-6-(p-metoxyphenyl)-8-benzylimidazo[1,2-a]pyrazyn-3-one [sic], 3,7-dihydro-2-methyl-6-(p-hydroxyphenyl)-8-benzylimidazo[1,2-a]pyrazyn-3-one [sic], 3,7-dihydro-2-phenyl-6-(p-hydroxyphenyl)-8-benzylimidazo[1,2-a]pyrazyn-3-one [sic], and 3,7-dihydro-2-benzyl-6-(p-hydroxyphenyl)-8-benzylimidazo[1,2-a]pyrazyn-3-one [sic].

* * * * *